United States Patent [19]

Ebitani et al.

[11] 4,265,788

[45] May 5, 1981

[54] ADSORBENT FOR SEPARATING PARA-XYLENE, AND PROCESS FOR THE PREPARATION THEREOF

[75] Inventors: Atsushi Ebitani, Kamakura; Takehisa Inoue, Tokyo; Kazuo Tsunoi, Kamakura, all of Japan

[73] Assignee: Toray Industries, Inc., Tokyo, Japan

[21] Appl. No.: 36,157

[22] Filed: May 4, 1979

[30] Foreign Application Priority Data

May 9, 1978 [JP] Japan ................................ 53-54735

[51] Int. Cl.³ .............................................. B01J 29/08
[52] U.S. Cl. ............................ 252/455 Z; 208/310 Z; 585/828
[58] Field of Search ................ 252/455 Z; 208/310 Z; 585/827, 828

[56] References Cited

U.S. PATENT DOCUMENTS

| | | | |
|---|---|---|---|
| 3,761,533 | 9/1973 | Otani et al. | 585/827 X |
| 3,793,386 | 2/1974 | Davis | 208/310 Z |
| 3,795,711 | 3/1974 | Worrell et al. | 208/310 Z |
| 4,069,172 | 1/1978 | Kanaoka et al. | 585/827 X |

*Primary Examiner*—Carl F. Dees
*Attorney, Agent, or Firm*—Miller & Prestia

[57] ABSTRACT

An adsorbent for separating para-xylene from $C_8$ aromatic hydrocarbons, specifically a faujasite zeolite which contains potassium, zirconium and proton or ammonium as cation, process for separating para-xylene, and process for making the adsorbent.

11 Claims, No Drawings

ADSORBENT FOR SEPARATING PARA-XYLENE, AND PROCESS FOR THE PREPARATION THEREOF

DESCRIPTION OF THE PRIOR ART

It is known that para-xylene can be separated by contacting $C_8$ aromatic hydrocarbons with faujasite zeolite containing certain selected cations. For example, Neuzil, U.S. Pat. No. 3,558,730 has disclosed that faujasite zeolite containing potassium and barium ions selectively adsorbs para-xylene over other $C_8$ aromatic hydrocarbons. Iwayama et al, in U.S. Pat. No. 4,069,172 have disclosed an adsorbent made by treating faujasite zeolite with an aqueous solution of an ammonium compound to exchange metal ions at cation sites with ammonium ions and drying, calcining and finally exchanging metal ions at cation sites with potassium and/or barium ions. Otani et al, in Japanese Patent Publication No. 8293/1977 have disclosed a faujasite zeolite containing potassium and at least one cation from the group of zirconium, yttrium, neodymium, lead, thorium, uranium and mercury.

SUMMARY OF THE INVENTION

It is an object of this invention to provide an improved adsorbent for separating para-xylene from $C_8$ aromatic hydrocarbons, to provide a process for preparation thereof, and to provide a novel process for carrying out said separation.

According to this description of the invention, it is to be understood that the phrase "$C_8$ aromatic hydrocarbons" is intended to mean a mixture which includes at least one other $C_8$ aromatic hydrocarbon in addition to the desired para-xylene. Such other hydrocarbon may be meta-xylene, ortho-xylene, ethylbenzene or any mixture thereof.

The manipulative steps of the various adsorptive separation processes are disclosed in Otani et al and also U.S. Pat. Nos. 3,686,342 and 3,626,020. The process of this invention also comprises two basic steps, the adsorption step and the desorption step. However, the separation step utilizes entirely different concepts in accordance with this invention.

In considering the adsorption step, the $C_8$ aromatic hydrocarbon feed mixture is contacted with an adsorbent which contains remaining desorbent material from a preceding cycle. As a result, para-xylene is selectively adsorbed on the adsorbent, displacing a part of the remaining desorbent, while a raffinate material is removed which consists of less selectively adsorbed components of the feed together with the displaced desorbent.

In the desorption step, the selectively adsorbed para-xylene on the adsorbent is displaced by desorbent. This leaves an extract which includes the desorbent and para-xylene. In adsorptive separation processes, the criterion used to determine the capability of a particular adsorbent for separating components of the feed is its selectivity, or its alpha value. Selectivity is defined with respect to two given components as the ratio of the concentration of the two components in the adsorbed phase divided by the ratio of the same two components in the unadsorbed phase which is in equilibrium with the adsorbed phase.

Selectivity for para-xylene over other $C_8$ aromatic hydrocarbons is defined by the following formula:

$$\alpha_{px/x} = \frac{(\text{wt. percent } px/\text{wt. percent } x)A}{(\text{wt. percent } px/\text{wt. percent } x)U} \quad (I)$$

wherein px is para-xylene, x is the other component; and A and U represent the adsorbed and unadsorbed phases, respectively. As the selectivity value approaches unity, there is no preferential adsorption of para-xylene. As selectivity becomes greater than unity there is preferential adsorption of para-xylene.

Desorbents which are preferred in this process are p-diethylbenzene or p-cymene. P-diethylbenzene is disclosed in U.S. Pat. No. 3,686,342 and p-cymene is disclosed in Ger. Offen. 2,783,518 (Miwa et al).

The selectivities of many crystalline aluminosiliate adsorbents have been examined by us in the presence of p-diethylbenzene or p-cymene, and we have discovered that selective adsorption in the presence of a faujasite zeolite which contains (a) potassium ions, (b) zirconium ions, and (c) hydrogen ions or ammonium ions, in combination with each other as cation, gives sharply and surprisingly improved results. That is, the absorbent of this invention has a higher selectivity for para-xylene over other $C_8$ aromatic hydrocarbons, and moreover the selectivity of para-xylene over the desorbent, such as para-diethylbenzene or para-cymene, approaches unity at the same time. This combination is outstanding from the viewpoint of overall and continuous effectiveness since the desorbent after displacing the para-xylene from the adsorbent is capable of being displaced on the adsorbent by the para-xylene of the feed in order to create a continuous process.

The faujasite zeolites utilized in the practice of this invention are commonly represented as types X and Y zeolite and is defined by the formula $0.9 \pm 0.2 Na_2O:Al_2O_3:2\text{-}6SiO_2:yH_2$, where y represents the degree of hydration.

Potassium, zirconium and hydrogen ion- or ammonium ion-exchange treatment may be performed by contacting a zeolite with an aqueous solution of a soluble salt of each cation. Potassium salts utilized in the ion-exchange treatment may include potassium salts of acids such as nitric acid, carbonic acid, hydrochloric acid or acetic acid, for example.

Zirconium compounds used in the ion-exchange treatment may include zirconyl-nitrate, zirconyl-acetate and other zirconyl compounds.

Compounds to be used in the hydrogen ion- or ammonium ion-exchange treatment may include inorganic or organic acids such as nitric acid, hydrochloric acid or acetic acid, for example, and ammonium salts such as ammonium nitrate, ammonium carbonate, ammonium sulfate and ammonium acetate, for example.

The degree of potassium cation exchange within the faujasite zeolite is 60 to 96% based in the total exchangeable cation sites originally present. The degree of zirconium ion-exchange within the faujasite zeolite is preferably about 2 to 25% based on the total exchangeable cation sites originally present, more preferably 5 to 20%. The degree of hydrogen or ammonium ion-exchange within the faujasite zeolite is preferably about 2 to 25% based on the total exchangeable cation sites originally present, more preferably 5 to 20%.

Adsorbents in accordance with this invention can be prepared, for example, using the following method.

Faujasite zeolite may be granulated, and then shaped zeolite may be contact with a solution containing potassium nitrate and/or zirconyl-nitrate and/or ammonium-nitrate. The ion-exchange treatment may be conducted in any order.

In another more preferable method, faujasite zeolite may be kneaded with a noncrystalline inorganic oxide, water and a zirconyl solution, and may be granulated to the required form. The resulting granule may be contacted with a solution containing both a potassium salt and an ammonium salt. The zeolite granule which contains potassium, zirconium and ammonium may be then dried and calcined.

Noncrystalline inorganic oxides for use in the practice of this invention may include, for example, alumina sol, silica sol, clay mineral and other minerals which contain amorphous silica and/or oxide of aluminum. This noncrystalline inorganic oxide is used preferably in an amount of about 1–30 wt% based on the faujasite zeolite.

Desorbents which can be used for para-xylene adsorptive separation in the process of this invention include various materials which have been disclosed in the prior art, preferably para-cymene and/or para-diethylbenzene. Para-cymene and para-diethylbenzene may be used individually or as a mixture. Para-cymene or para-diethylbenzene may be used as admixtures of isomers, such as meta-cymene, ortho-cymene, meta-diethylbenzene or ortho-diethylbenzene, for example. The desorbent may also be used with a diluent including a paraffinic hydrocarbon and/or cycloparaffins or mixtures thereof.

In accordance with the process of the present invention, adsorptive separation should be performed at a temperature from about zero to about 350° C., preferably from about 30° C. to about 250° C., and under a pressure of about atmospheric pressure to 30 kg/cm². Although in theory both liquid and vapor phase operations may be contemplated for carrying out the separatory process of the present invention, in practice it has been found preferable to utilize liquid phase separation in order to prevent undesirable reactions that may occur in high temperature operations, such as in the vapor phase. It is contemplated in accordance with the process of the present invention that both the raffinate and extract streams can be passed into respective fractionating facilities so that the extract stream may be separated into a relatively pure desorbent stream and a relatively pure para-xylene stream. The raffinate stream can similarly be passed into a fractionating facility in which the raffinate material can be separated into a concentrated stream of desorbent material and the less selectively adsorbed feed components. It is contemplated that in accordance with the present invention the relatively purified desorbent stream from both the raffinate and the extract stream may be reused in the process. The raffinate stream comprising the less selectively adsorbed components of the feed can be passed into an isomerization zone in which isomerization takes place in order to produce additional amounts of para-xylene. The combination of isomerization and adsorptive separation processes thus allows the possibility of an increased yield of the desired para-xylene from the feed stock based upon the quantity of the $C_8$ aromatic hydrocarbon feed.

In testing various adsorbents in the following examples, the selectivity of the adsorbent in the presence of the desorbent was determined using a static testing apparatus using procedures which are described in more detail below. The static testing apparatus had a volume of 5 ml. and was made of stainless steel. 2 gm. of feed containing a mixture of $C_8$ aromatic hydrocarbons and desorbent, and 2 gm. of adsorbent were fed into the apparatus. It was then stoppered and placed into an oil bath, at a temperature of 175° C. for one hour until adsorption reached an equilibrium condition. The liquid in the apparatus was sampled with a microsyringe and analyzed with gas chromatography. Selectivity was calculated as previously defined herein.

The following Examples are illustrative, but are not intended to define or to limit the scope of the invention, which is defined in the appended claims.

EXAMPLE 1

420 grams of sodium form type Y zeolite (water content 17 wt%) were mixed with 175 grams of alumina sol ($Al_2O_3$ content 10 wt%), 130 grams of water and an aqueous solution of zirconyl nitrate ($ZrO_2$ content 25 wt%). To prepare various adsorbents, the weight of the zirconyl nitrate solution was varied. The mixture was kneaded into a stiff paste. The paste was extruded into small particles, which were then dried at 100° C. for 16 hours, and calcined at 500° C. for one hour. The (Na, Zr)Y zeolite particle which was obtained preferably was subjected to ion-exchange treatment with an aqueous solution which contained potassium nitrate and ammonium nitrate until the residual sodium ion concentration within the zeolite dropped to less than 0.05 equivalent. To prepare various adsorbents, the ammonium nitrate concentrations of the ion-exchange aqueous solutions were varied and a constant concentration of potassium nitrate of 7.0 wt% was used. After completing the ion-exchange treatment, the adsorbent was dried at 120° C. for 6 hours and then calcined at 500° C. for one hour. In order to evaluate the performances of these adsorbents in the process of the present invention, the selectivity for para-xylene was determined by the procedure previously described.

The feed mixture used for these tests had the following composition:

| Normal nonane | (n-$C_9$) | 1 part by weight |
|---|---|---|
| Para-xylene | (PX) | 1 part by weight |
| Meta-xylene | (MX) | 1 part by weight |
| Ortho-xylene | (OX) | 1 part by weight |
| Ethylbenzene | (EB) | 1 part by weight |
| Para-cymene | (D) | 5 parts by weight |

Upon the assumption that n-$C_9$ was not adsorbed, the selectivity values were calculated using the aforementioned formula. The results are set forth in Table 1 which follows.

COMPARATIVE EXAMPLE 1

420 grams of sodium form type Y zeolite (water content 17 wt%) were mixed with 175 grams of alumina sol ($Al_2O_3$ content 10 wt%), 130 grams of water and 57 grams of zirconyl nitrate aqueous solution ($ZrO_2$ content 25 wt%). The mixture was kneaded and then extruded into small particles, which were then dried at 100° C. for 16 hours and calcined at 500° C. for one hour. The (Na,Zr)Y zeolite particle which was obtained was subjected to ion-exchange treatment with an aqueous solution of potassium nitrate. After completing the ion-exchange treatment, the adsorbent was dried at 120° C. for 6 hours and calcined at 500° C. for one hour. In this manner, a (K,Zr)Y zeolite adsorbent was prepared.

In separate tests 420 grams of sodium form type Y zeolite (water content 17 wt%) were mixed with 175 grams of alumina sol (Al$_2$O$_3$ content 10 wt%) and 160 grams of water. The mixture was kneaded and extruded into small particles, which were then dried at 100° C. for 16 hours and calcined at 500° C. for one hour. The NaY zeolite particle which was obtained was subjected to ion-exchange treatment with an aqueous solution of potassium nitrate or a mixed solution of potassium nitrate and ammonium nitrate. After completing the ion-exchange treatment, the adsorbent was dried at 100° C. for 6 hours and calcined at 500° C. for one hour, and KY zeolite and (K, NH$_4$)Y zeolite adsorbents were prepared.

Each of these adsorbents was tested to determine selectivity by the procedure used in Example 1. The results are set forth in Table 1. In order to evaluate the performances of these adsorbents, the selectivity of para-xylene especially against ethylbenzene and para-cymene should be noted as set forth in Table 1 which follows.

Adsorbents used in runs numbered 1–10 in Table 1 are (K, NH$_4$,ZR)Y zeolite adsorbents, and numbers 1–5 are runs in which the degree of zirconyl ion-exchange was varied. Numbers 6–10 are examples in which the extent of ammonium ion-exchange treatment was varied.

Adsorbents used in runs 11–13 are adsorbents of the prior art utilizing potassium Y zeolite, potassium zirconium, Y zeolite and potassium ammonium zeolite. The data of runs 11–13 show that zirconium (run 11) is effective to increase the value of $\alpha$PX/EB but decreases $\alpha$PX/D, and ammonium (run 12) is effective to increase the values of both $\alpha$PX/EB and $\alpha$PX/D.

It is also demonstrated in Table 1 that adsorbents containing both zirconium and ammonium (runs 1–10) have higher $\alpha$PX/EB values and more desirable $\alpha$PX/D values. It is shown from the data of runs 1–3 and 12 that the value of $\alpha$PX/EB increases with increase of degree of zirconium ion-exchange but runs 4 and 5 show that the values of $\alpha$PX/EB and $\alpha$PX/D decrease when the degree of zirconium ion-exchange is above 25%. It is shown from the data of runs 6–11 that the value of $\alpha$PX/D increases with increased degree of ammonium ion-exchange, that when the degree of ammonium ion-exchange is increased about to 25%, the value of $\alpha$PX/D approaches unity, but that when the degree of ammonium ion-exchange is further increased to a value above 25%, the value of $\alpha$PX/D is far from unity, and moreover, the value of $\alpha$PX/EB decreases markedly.

TABLE 1

| No. | Adsorbent | Cation Composition (%) | | | Selectivity | | | |
|---|---|---|---|---|---|---|---|---|
| | | K | Zr | NH$_4$ | PX/EB | PX/MX | PX/OX | PX/D |
| 1 | (K,Zr,NH$_4$)Y | 85 | 5 | 10 | 2.13 | 3.06 | 2.71 | 0.76 |
| 2 | (K,Zr,NH$_4$)Y | 80 | 10 | 10 | 2.24 | 3.41 | 2.99 | 0.72 |
| 3 | (K,Zr,NH$_4$)Y | 75 | 15 | 10 | 2.25 | 3.53 | 3.09 | 0.76 |
| 4 | (K,Zr,NH$_4$)Y | 65 | 25 | 10 | 2.15 | 3.18 | 2.82 | 0.71 |
| 5 | (K,Zr,NH$_4$)Y | 60 | 30 | 10 | 2.06 | 2.99 | 2.69 | 0.71 |
| 6 | (K,Zr,NH$_4$)Y | 80 | 15 | 5 | 2.17 | 3.50 | 3.07 | 0.72 |
| 7 | (K,Zr,NH$_4$)Y | 70 | 15 | 15 | 2.20 | 3.21 | 2.76 | 0.81 |
| 8 | (K,Zr,NH$_4$)Y | 65 | 15 | 20 | 2.08 | 2.82 | 2.37 | 0.91 |
| 9 | (K,Zr,NH$_4$)Y | 60 | 15 | 25 | 1.96 | 2.35 | 1.91 | 1.02 |
| 10 | (K,Zr,NH$_4$)Y | 55 | 15 | 30 | 1.81 | 1.92 | 1.50 | 1.18 |
| 11 | (K,Zr)Y | 85 | 15 | 0 | 2.15 | 3.44 | 3.01 | 0.68 |
| 12 | (K,NH$_4$)Y | 90 | 0 | 10 | 2.08 | 3.04 | 2.62 | 0.84 |
| 13 | KY | 100 | 0 | 0 | 1.98 | 3.11 | 2.71 | 0.72 |

COMPARATIVE EXAMPLE 2

420 grams of sodium-form type Y zeolite (water content 17 wt%) were mixed with 175 grams of alumina sol (Al$_2$O$_3$ content 10 wt%), 160 grams of water and 20.2 grams of barium nitrate or 19.8 grams of yttrium nitrate. The mixture was kneaded and then extruded into small particles, which were then dried at 100° C. for 16 hours and calcined at 500° C. for one hour. The (Na,Ba)Y or (Na,Y)Y zeolite which was obtained was subjected to ion-exchange treatment and then dried, and was calcined using the method described in Example 1. These two adsorbents were tested to determine selectivity by the procedures used in Example 1. The results are set forth in Table 2.

TABLE 2

| No. | Adsorbent | Cation Composition % | | | Selectivity | | | |
|---|---|---|---|---|---|---|---|---|
| | | K | Ba/Y | NH$_4$ | PX/EB | PX/MX | PX/OX | PX/D |
| 14 | (K,Ba,NH$_4$)Y | 80 | 10 | 10 | 2.05 | 3.26 | 2.75 | 0.68 |
| 15 | (K,Y,NH$_4$)Y | 80 | 10 | 10 | 2.00 | 2.93 | 2.53 | 0.81 |

Accordingly, it is important to provide an adsorbent wherein the degree of cation exchange, for the zirconium ion, is about 2–25% of the total exchangeable cation sites originally present, and for the ammonium ion about 2–25%, of the total cation sites originally present. Further, it is important to provide K ion in exchange of about 60–96% on the same basis.

We claim:

1. An adsorbent for separating para-xylene from C$_8$ aromatic hydrocarbons, comprising a faujasite zeolite which contains:
   (a) potassium ion;
   (b) zirconium ion; and
   (c) hydrogen ion or ammonium ion as cations.

2. The adsorbent according to claim 1, wherein said cations are cation exchanged and wherein the degree of cation exchange for each cation is:
   K About 60–96%
   Zr About 2–25% and
   H or NH$_4$ About 2–25%, based on the total exchangeable cation sites originally present.

3. The adsorbent according to claim 2, wherein the Zr percentage is about 5–20.

4. The adsorbent accoridng to claim 2, wherein the H or $NH_4$ percentage is about 5–20.

5. In a process for preparing a faujasite zeolite adsorbent which is useful for separating para-xylene from $C_8$ aromatic hydrocarbons, the steps which comprise granulating and simultaneously kneading a faujasite zeolite with a noncrystalline inorganic oxide and a solution of zirconyl compound in a manner to effect zirconium ion exchange therewith and ion-exchange treating the product with potassium ions and with hydrogen or ammonium ions.

6. The process defined in claim 5 wherein the zirconium ion exchange treatment is provided in an amount up to about 2–25% Zr.

7. The process defined in claim 6, the percentage being about 5–20% Zr.

8. The process defined in claim 5, wherein the ammonium ion exchange treatment is provided up to about 2–25% H or $NH_4$ ion.

9. The process as defined in claim 5, wherein the zirconium ion exchange treatment is provided in an amount up to about 5–20% H or $NH_4$.

10. The process as defined in claim 5, wherein the zirconium ion and ammonium ion treatment is provided in an amount up to about 5–25% Zr and $NH_4$ ion exchange each.

11. The process as defined in claim 10, said percentages being 5–20%.

* * * * *

UNITED STATES PATENT AND TRADEMARK OFFICE
CERTIFICATE OF CORRECTION

PATENT NO. : 4,265,788
DATED : May 5, 1981
INVENTOR(S) : Atsushi Ebitani et al.

It is certified that error appears in the above—identified patent and that said Letters Patent is hereby corrected as shown below:

Column 5, line 35, delete "$(K,NH_4ZR)Y$" and insert --$(K,NH_4Zr)Y$--.

Column 8, line 14, delete "5-25%" and insert --2-25%--.

Signed and Sealed this

Third Day of November 1981

[SEAL]

Attest:

GERALD J. MOSSINGHOFF

Attesting Officer     Commissioner of Patents and Trademarks